(12) United States Patent
Meskens et al.

(10) Patent No.: US 9,950,163 B2
(45) Date of Patent: Apr. 24, 2018

(54) CONFIGURATION OF HEARING DEVICE COMPONENTS

(71) Applicant: Cochlear Limited, Macquarie University, NSW (AU)

(72) Inventors: Werner Meskens, Opwijk (BE); Mark Alan von Huben, Waverton (AU)

(73) Assignee: Cochler Limited, Macquarie University, NSW (AU)

( * ) Notice: Subject to any disclaimer, the term of this patent is extended or adjusted under 35 U.S.C. 154(b) by 0 days.

(21) Appl. No.: 15/160,024

(22) Filed: May 20, 2016

(65) Prior Publication Data

US 2017/0056656 A1    Mar. 2, 2017

Related U.S. Application Data

(60) Provisional application No. 62/210,743, filed on Aug. 27, 2015.

(51) Int. Cl.
*A61N 1/36*    (2006.01)
*A61N 1/372*   (2006.01)
*A61N 1/375*   (2006.01)

(52) U.S. Cl.
CPC ..... *A61N 1/36032* (2013.01); *A61N 1/36036* (2017.08); *A61N 1/3754* (2013.01); *A61N 1/37229* (2013.01)

(58) Field of Classification Search
None
See application file for complete search history.

(56) References Cited

U.S. PATENT DOCUMENTS

| 7,072,718 B2 * | 7/2006 | Von Arx | A61N 1/37229 607/32 |
| 8,050,771 B2 * | 11/2011 | Yamamoto | A61N 1/37229 607/60 |
| 2011/0137377 A1 | 6/2011 | Daly et al. | |
| 2011/0266713 A1 | 11/2011 | Vincent et al. | |
| 2012/0194981 A1 | 8/2012 | Kempf et al. | |
| 2015/0088226 A1 | 3/2015 | Tourrel et al. | |
| 2015/0163603 A1 | 6/2015 | Christensen et al. | |

OTHER PUBLICATIONS

International Search Report and Written Opinion from International Application No. PCT/IB2016/054930, dated Nov. 30, 2016.

* cited by examiner

*Primary Examiner* — Brian T Gedeon

(57) ABSTRACT

Disclosed herein are example configurations of implantable units of implantable medical devices such as hearing devices. An example implantable hearing device includes a housing having a posterior side and an anterior side, with the anterior side being formed such that an inner edge of the anterior side defines an aperture. The housing includes an electrical feedthrough, a transceiver, and an antenna element. The electrical feedthrough is made of one or more biocompatible materials, and at least a portion of the electrical feedthrough is positioned beneath the aperture. The transceiver is configured to conduct RF communications. Further, the antenna element is electrically connected to the transceiver and is positioned below, above, or inside the electrical feedthrough.

27 Claims, 10 Drawing Sheets

CONFIGURATION OF HEARING DEVICE COMPONENTS

REFERENCE TO RELATED APPLICATION

This application claims priority to U.S. Provisional Patent Application No. 62/210,743, filed Aug. 27, 2015, the entirety of which is hereby incorporated by reference.

BACKGROUND

Various types of hearing devices provide people with different types of hearing loss with the ability to perceive sound. Hearing loss may be conductive, sensorineural, or some combination of both conductive and sensorineural. Conductive hearing loss typically results from a dysfunction in any of the mechanisms that ordinarily conduct sound waves through the outer ear, the eardrum, or the bones of the middle ear. Sensorineural hearing loss typically results from a dysfunction in the inner ear, including the cochlea where sound vibrations are converted into neural signals, or any other part of the ear, auditory nerve, or brain that may process the neural signals.

People with some forms of conductive hearing loss may benefit from hearing devices such as hearing aids or electromechanical hearing devices. A hearing aid, for instance, typically includes at least one small microphone to receive sound, an amplifier to amplify certain portions of the received sound, and a small speaker to transmit the amplified sounds into the recipient's ear. An electromechanical hearing device, on the other hand, typically includes at least one small microphone to receive sound and a mechanism that delivers a mechanical force to a bone (e.g., the recipient's skull, or a middle-ear bone such as the stapes) or to a prosthetic (e.g., a prosthetic stapes implanted in the recipient's middle ear), thereby causing vibrations in cochlear fluid.

Further, people with certain forms of sensorineural hearing loss may benefit from hearing devices such as cochlear implants and/or auditory brainstem implants. Cochlear implants, for example, include at least one microphone to receive sound, a unit to convert the sound to a series of electrical stimulation signals, and an array of electrodes to deliver the stimulation signals to the recipient's cochlea so as to help the recipient perceive sound. Auditory brainstem implants use technology similar to cochlear implants, but instead of applying electrical stimulation to a recipient's cochlea, they apply electrical stimulation directly to a recipient's brain stem, bypassing the cochlea altogether while still helping the recipient perceive sound.

In addition, some people may benefit from hearing devices that combine one or more characteristics of the acoustic hearing aids, vibration-based hearing devices, cochlear implants, and/or auditory brainstem implants to perceive sound.

Hearing devices such as these typically include an external processing unit that typically performs at least some sound-processing functions and an internal stimulation unit that at least delivers a stimulus to a body part in an auditory pathway of the recipient. The auditory pathway includes a cochlea, an auditory nerve, a region of the recipient's brain, or any other body part that contributes to the perception of sound. In the case of a totally-implantable hearing device, the stimulation unit includes both processing and stimulation components, though the external unit may still perform some processing functions when communicatively coupled or connected to the stimulation unit.

SUMMARY

Many modern hearing devices are configured to communicate with external devices via a wireless communication link, which is often a radio frequency (RF) link. By way of example, a hearing device may be configured to wirelessly receive audio streams from a media device, such as a smartphone, a tablet computer, a laptop computer, a television, a personal media player, and the like. Additionally or alternatively, the hearing device may communicate with a remote programming or diagnostic device, thereby providing the recipient with the ability to adjust sound settings, such as a volume of perceived sounds, a sound processing program, etc. The hearing device might also be a component of a bilateral hearing device system in which the recipient wears a hearing device on each side of the recipient's head. In this example, the hearing devices may wirelessly exchange audio and/or control data via an RF communication link.

To this end, the hearing device may include communication equipment for conducting short-range RF communications (e.g., a Bluetooth® transceiver or a Wi-Fi® transceiver). In a partially-implantable prosthesis, an external unit of the hearing device may include a transceiver and an antenna element for RF communications. Incorporating RF communication components into an implantable unit of a hearing device may be more complicated. Unlike the external unit of an implantable hearing prosthesis, the communication components of an implantable unit of the hearing device are usually included in a hermetically-sealed housing made of one or more biocompatible metals that may significantly attenuate RF signals. Thus, locating the antenna into the housing may limit the distance over which the implantable portion of the hearing device can reliably communicate unit with an external device.

The present disclosure provides systems and devices for improving the reliability and range of wireless communications between an implantable portion of a hearing device and external devices. In accordance with the disclosure, the implantable portion of the hearing device includes a hermetically-sealed metallic housing that includes a biocompatible feedthrough in, near, or under an aperture defined in at least one side. The housing is formed from a biocompatible metal, such as titanium. The feedthrough, which includes the conductive signal paths for electrically connecting stimulation electrodes and/or an acoustic actuator, is made of a biocompatible insulation material (i.e. ceramic material) that is quasi transparent or lossless for RF signals. The housing also includes an antenna and/or one or more antenna elements that are positioned beneath, level with, or slightly above the feedthrough and in-line with the aperture in the housing. Positioning the antenna (or at least one antenna element) beneath the aperture may reduce the attenuation of RF signals transmitted and received via the antenna, thereby providing more reliable RF communications between the implantable portion of the hearing prosthesis and external devices.

The housing and/or components included in the housing may be adapted to further improve the quality of RF communications conducted by the implantable portion of the hearing device. As one example, a waveguide can be positioned in or beneath the aperture, thereby channeling RF signals into and out of the antenna or antenna elements. In another example a feedthrough, which electrically connects one or more stimulators to a stimulation-generating component included in the housing, can comprise one or more materials that are good conductors of RF signals, at least as compared to the materials of the housing's exterior. The feedthrough can be positioned between the aperture and the antenna (or at least one antenna element), and the feedthrough can thus act as a waveguide. Further, the feedthrough can have a curved surface that functions like a lens for RF signals by focusing incoming RF signals into the antenna element and dispersing outgoing RF signals over a wider range of directions (as compared to a feedthrough without a curved surface). And as yet another example, the feedthrough can include one or more dielectric materials, which could improve the conduction of RF signals through the feedthrough and/or cause the feedthrough to function like a waveguide. In a similar manner, the housing's exterior around the aperture may be shaped to act as a waveguide for RF signals.

Accordingly, in one aspect an implantable medical device is disclosed. The implantable medical device includes a housing having a side defining an aperture, and an electrical feedthrough made of one or more biocompatible materials that covers the aperture to form a hermetic enclosure within the housing. Further, the implantable medical device includes a receiver (e.g., part of a transceiver) configured to conduct RF communications, and an antenna element electrically connected to the receiver and positioned in-line (e.g., below, above, or inside) the electrical feedthrough.

In another aspect, a hearing prosthesis is disclosed. The hearing prosthesis includes a housing and an electrode array implantable in a cochlea. The electrode array includes a plurality of electrodes. The housing has an aperture that is sealed by an electrical feedthrough to form a hermetic enclosure. The electrical feedthrough connects the electrodes to electronic circuitry disposed within the hermetic enclosure. A radio frequency (RF) transceiver is also housed within the hermetic enclosure and electrically connected to one or more antenna elements. Each antenna element is positioned in-line with the aperture.

In another aspect, an implantable medical device is disclosed. The implantable medical device comprises a hermetic enclosure that encases electronic circuitry, including a radio frequency transceiver. The hermetic enclosure comprises a metallic chassis with an aperture sealed by a non-metallic feedthrough. The radio frequency transceiver has an antenna element that is disposed in-line with the aperture. The antenna element can be disposed within the hermetic enclosure or outside the hermetic enclosure. It can also be embedded within the feedthrough so that it is substantially level with the aperture.

These as well as other aspects and advantages will become apparent to those of ordinary skill in the art by reading the following detailed description, with reference where appropriate to the accompanying drawings. Further, it is understood that this summary is merely an example and is not intended to limit the scope of the invention as claimed.

DETAILED DESCRIPTION

Figure 1:
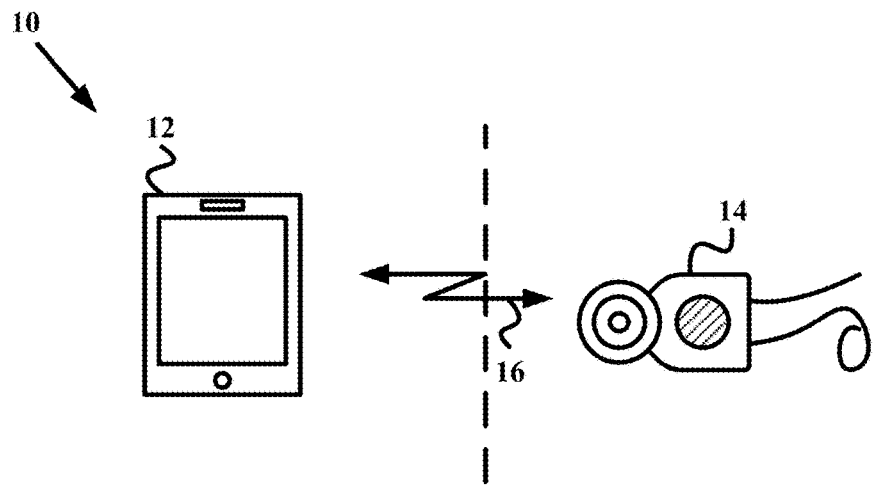
FIG. 1 is a simplified diagram of an example system in which features of the present disclosure can be implemented.

Referring to the drawings, as noted above, FIG. 1 is a simplified diagram of a system 10 in which features of the present disclosure can be implemented. As shown, the system 10 includes an external device 12 and an implantable unit of a hearing device 14. In FIG. 1, the external device 12 is depicted as a smartphone, but the external device 12 could also be a tablet computer, a portable music player, a laptop computer, or the like. Further, the external device 12 could be a behind-the-ear sound processor, a button sound processor, or another hearing device, such as when the hearing device 14 is part of a bilateral hearing device system. The external device 12 could communicate with the hearing device 14 via a wireless link 16, such as a short-range radio frequency link (e.g., a Bluetooth® link, a Wi-Fi link, or any proprietary link).

Figure 2:
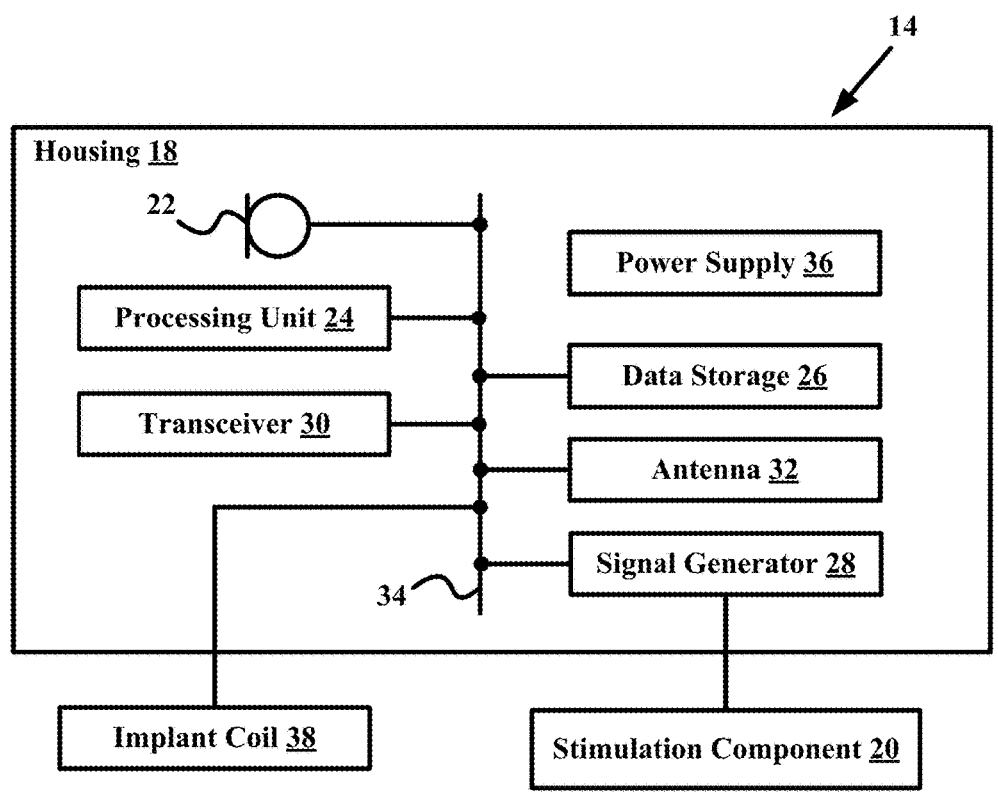
FIG. 2 is a block diagram depicting components of an example an implantable unit of a hearing device.

In the illustrated example, the hearing device 14 is a totally-implantable cochlear implant. FIG. 2 is a block diagram of such a hearing device in an example implementation. As shown, the hearing device 14 includes a hermetically-sealed housing 18, a stimulation component 20, and a microphone (or another audio transducer) 22. The stimulation component 20 may include a plurality of electrodes mounted on an electrode array, and the electrode array may be surgically implanted in a recipient's cochlea. In an example in which the hearing device 14 is not a cochlear implant, the stimulation component 20 may include a different electrical stimulator, or perhaps an electro-mechanical stimulator, an acoustic stimulator, and/or a combination of stimulators.

Within the hermetic enclosure defined by the housing 18 are a processing unit 24, a data storage 26, a signal generator 28, a transceiver 30, and an antenna 32, which are communicatively linked together by a system bus, network, or other connection mechanism 34. The housing 18 may also include a power supply 36, such as a rechargeable battery, that is configured to provide power to the components of the hearing device 14 when power is not supplied by an external power source (e.g., a device configured to at least inductively charge the power supply 36). The housing 18 may also include a coil 38 for recharging the power supply 36 and/or for providing power to the components of the hearing device 14, as well as for receiving externally-processed sounds from an externally-worn sound processing unit.

In the illustrated arrangement, the microphone 22 could be positioned to receive audio input from an acoustic environment, and to provide a corresponding signal (e.g., electrical or optical, possibly sampled) to the processing unit 24. Further, the microphone 22 could include additional microphones and/or other audio transducers, which could also be positioned in the recipient's body to receive sounds from the ambient environment, or which could be positioned to receive internal sounds from the recipient's organs. As one example, the microphone 22 could be replaced with a transducer that detects a movement of one or more ossicles bones in the recipient's ear.

In an example operation, the processing unit 24 generates stimulation signals by processing sound signals received from the microphone 22 or from an external device. To this end, the processing unit 24 could include one or more sound processors and could access reference data and/or program instructions stored in the data storage 26. The processing unit 24 could send each stimulation signal to the signal generator 28. The signal generator 28 could in turn generate an electrical signal sent to each of one or more electrodes of the stimulation component 20. And the electrode(s) could then deliver one or more electrical stimuli to the recipient's cochlea, thereby enabling the recipient to perceive a portion of a sound.

As described above, the hearing device 14 could receive audio signals (or perhaps other signals) from the external device 12. In particular, the transceiver 30 could be configured to send via the antenna element 32 RF signals to and receive signals from the external device 12. By way of example, the transceiver 30 and the antenna 32 may thus be configured to enable RF communications via the link 16. As such, the antenna 32 could comprise any suitable metal or alloy suitable for RF communications, such as platinum. Further, while one antenna is shown in FIG. 2, the housing 18 could include one or more antenna elements in addition to or in lieu of the antenna 32.

Figure 3:
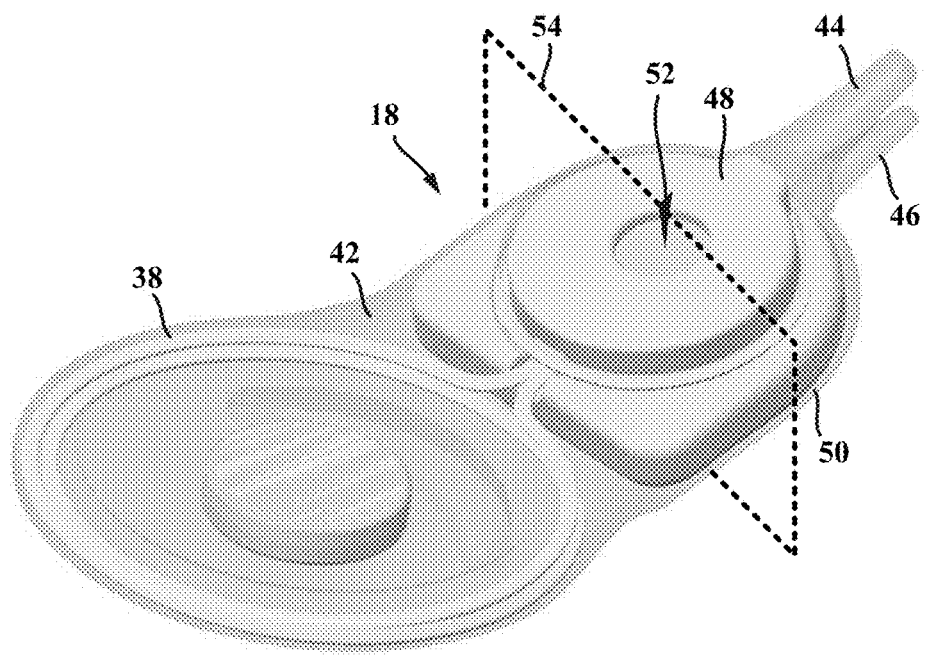
FIG. 3 is a perspective view of an example implantable unit of a hearing device.

In accordance with the disclosure, an external structure of the housing 18 could be configured to facilitate RF communications. FIG. 3 is a perspective view of one embodiment of the hearing device 14. As shown, a biocompatible polymer covering 42 covers the housing 18, as well as the coil 38 and stimulation component leads 44 and 46, in order prevent biofilm growth on components of the hearing device 14 and/or tissue damage during implantation. The illustrated housing 18 comprises a metallic chassis and a non-metallic feedthrough 52 that covers an aperture in the metallic chassis. The feedthrough 52 hermetically seals the housing and facilitates electrical communication with components disposed outside the hermetic enclosure, such as the electrodes of an electrode array. The antenna for the RF transceiver is disposed in-line (i.e. above, within or below) the non-metallic feedthrough to reduce the influence of the metallic chassis on RF signal strength. Further, a surface of the antenna (e.g., of one or more antenna elements) could be in physical contact with a surface of the feedthrough.

The implant shown in FIGS. 3 to 19 is a hearing prosthesis, or more specifically, the stimulator unit for a cochlear implant. However, the general disclosure of this specification is also applicable to other implantable medical devices, such as active bone conduction devices, pace makers and neural stimulators. The same implant chassis and feedthrough layout is used in each of the Figures for clarity so that the variations described in the text are isolated and readily identifiable. The fundamental principles disclosed in this specification are equally applicable to other chassis/feedthrough layouts, such as chassis with multiple apertures/feedthroughs disposed in close proximity, chassis with the aperture/feedthrough disposed in a side wall and elongate apertures/feedthroughs layouts.

The housing 18 is shown having an anterior plate 48 and a posterior plate 50, with the posterior plate 50 being the closer of the two plates 48, 50 to the recipient's skull after implantation. Each of the anterior plate 48 and the posterior plate 50 could be made from a biocompatible metal (e.g., titanium) or another biocompatible material. By way of example, each of the anterior plate 48 and the posterior plate 50 could be about 0.25 millimeters thick. Additionally, an upper surface of the anterior plate 48 could have a diameter of about 15 millimeters, whereas the posterior plate 50 could, in contrast, have a maximum width/effective diameter of about 22 millimeters.

In line with the discussion above, the anterior plate 48 could be formed such that an inner edge 66 defines an aperture 52, with the aperture 52 being about 5 millimeters in diameter. The inner edge of the anterior plate 48 (e.g., the edge that defines the aperture 52) could extend axially into the housing from the upper surface to a depth of about 0.8 millimeters below the upper surface of the anterior plate 48. The aperture 52 could thus provide a quasi-transparent signal path for RF signals transmitted and received via the antenna 32. Positioning the antenna 32 beneath the aperture 52 may thus allow for more reliable communications between the implantable unit 14 and an external device, as at least a portion of an RF signal can reach or leave the antenna element 32 without passing through the lossy material of the anterior side 48.

The particular arrangement of the components included in the housing 18 can take a number of forms. For instance, the housing 18 can include a feedthrough for electrically connecting components of the stimulation component to the signal generator 28 via a printed circuit board 56, with the printed circuit board 56 being a component of the connection mechanism 34. The feedthrough 58 can comprise a material, such as a ceramic material, that is biocompatible and is transparent to, or perhaps even a good director of RF signals. FIGS. 4-13 show example cross-sections of the housing 18 (as indicated by the dashed box 54 in FIG. 3) in which the feedthrough is positioned in-line with the aperture 52 and between the antenna element 32 and the anterior plate 48. It is noted that the relative dimensions in FIGS. 4-13 and other Figures in this disclosure are not necessarily to scale, but have been rendered for purposes of explanation only in describing the arrangement of substrates, structures, and devices described herein.

Figure 4:
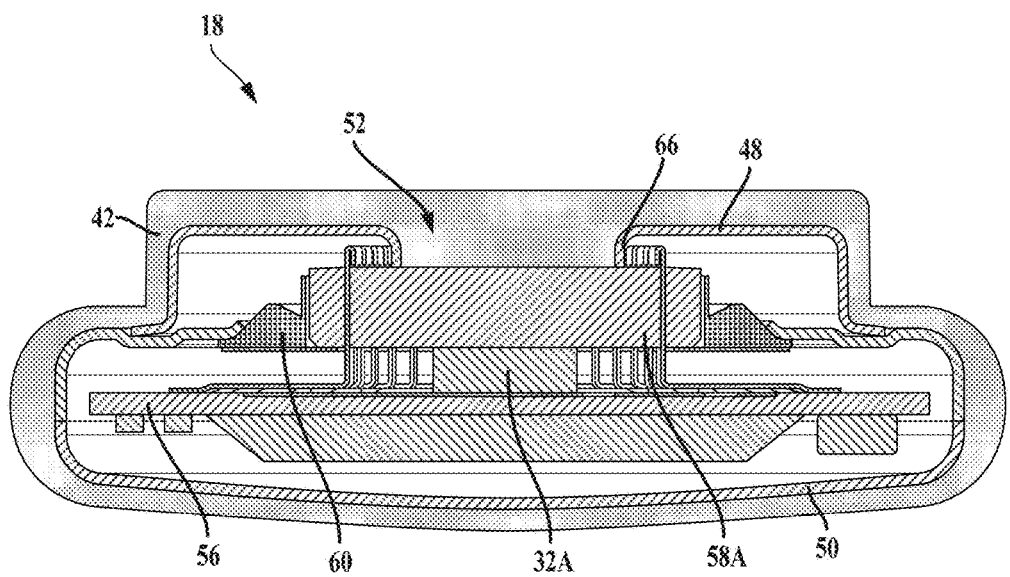
FIGS. 4-19 are example cross-sections of the implantable unit depicted in FIG. 3.

Beginning with FIG. 4, a first antenna 32A may be mounted on a printed circuit board 56, which could be a component of the connection mechanism 34. The illustrated feedthrough 58A is supported by a ring 60 such that the first feedthrough 58A is positioned above the first antenna 32A and below the aperture 52. The ring 60 could also include contacts for electrically connecting the conductive path elements in the first feedthrough 58A (as well as other feedthroughs described herein). Other structures can be used within the housing to support the feedthrough.

Figure 5:
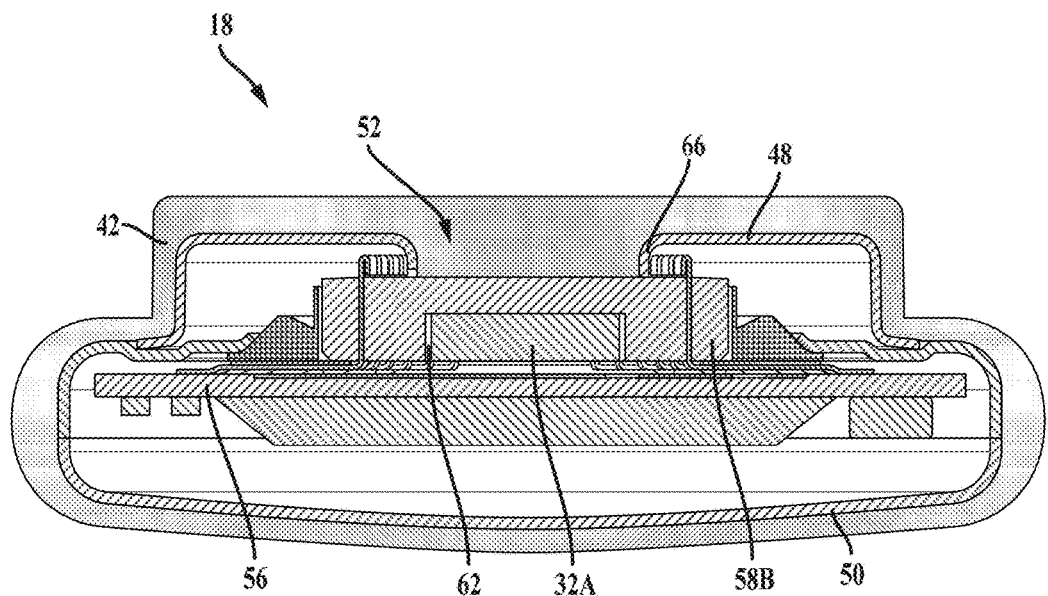

In FIG. 5, a second feedthrough 58B is mounted on the printed circuit board 56. The second feedthrough 58B is formed so as to define a recess 62 in a posterior surface of the second feedthrough 58B, thereby allowing the second feedthrough 58B to be mounted over and around the first antenna element 32A.

Figure 6:
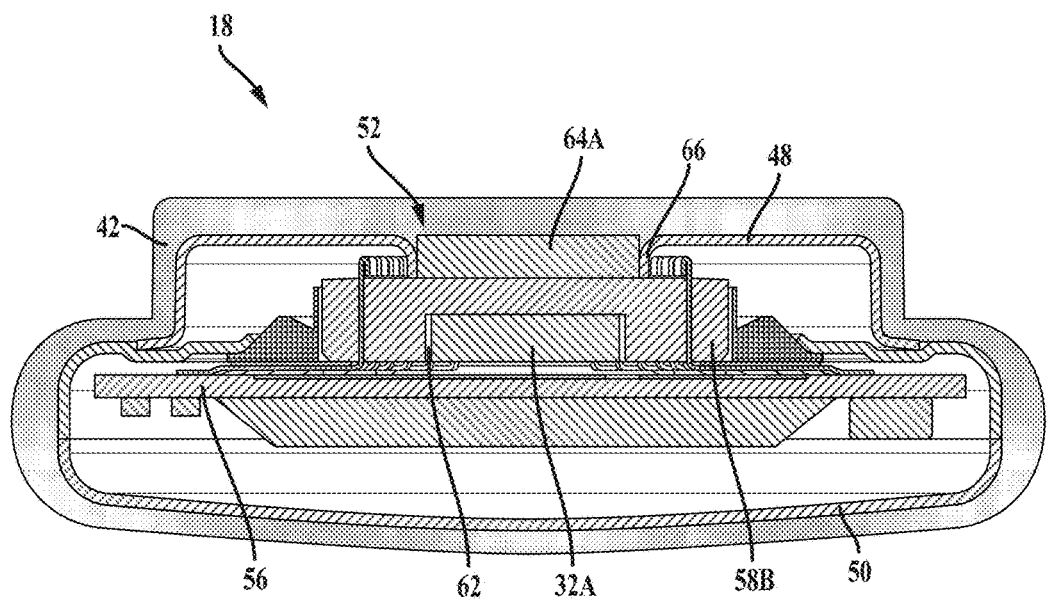
Figure 7:
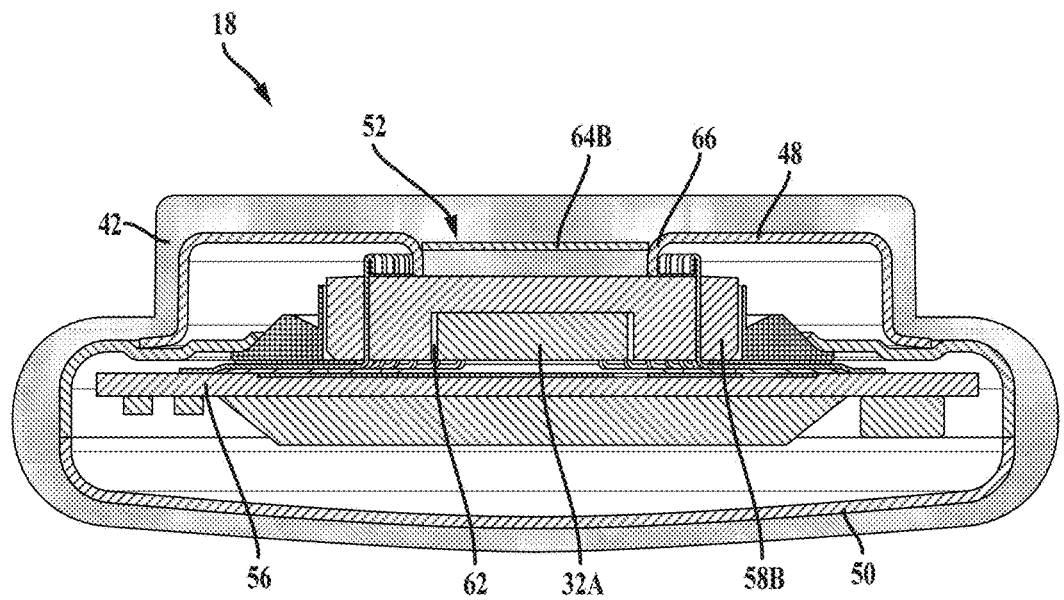

To improve communications between the implantable unit 14 and the external device 12, a waveguide could be positioned in the aperture 52 over the feedthrough. Using a waveguide may reduce the directionality of the antenna element 32. FIGS. 6 and 7 show two examples in which a waveguide is positioned above the second feedthrough 58B. In FIG. 6, a first waveguide 64 is mounted on the second feedthrough 58B and extends upward such that an upper surface of the first waveguide 64A is level with the upper surface of the anterior plate 48. Alternatively, a thinner second waveguide 64B could be used, as shown in FIG. 7. In this example, the second waveguide 64B is suspended in the polymer covering 42 such that the second waveguide 64B is level with upper surface of the anterior plate 48. Both waveguides 64A and 64B could be made of any suitable biocompatible material, with the first waveguide 64A having a thickness of about 0.8 millimeters and the second waveguide 64B having a thickness of about 0.1 millimeter.

Figure 8:
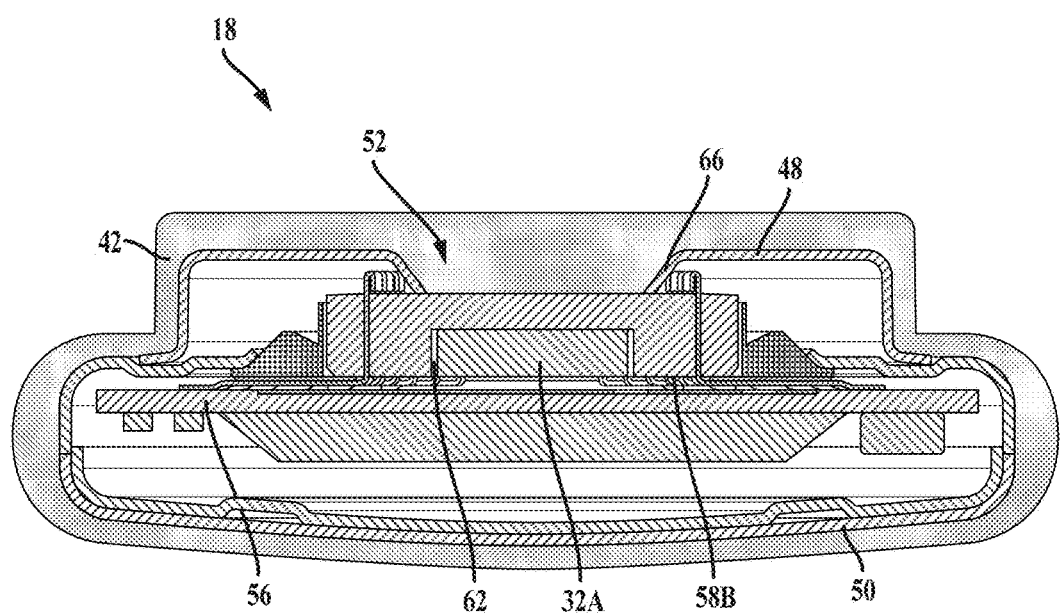

In other examples, components of the housing 18 could be shaped to act as a waveguide. For example, the inner edge 66 of the anterior plate 48 could be angled toward the center of the aperture 52, as shown in FIG. 8. In this manner, the portion 66 of the anterior plate 48 can act as a waveguide for RF signals going into and coming out of the antenna element 32.

Figure 9:
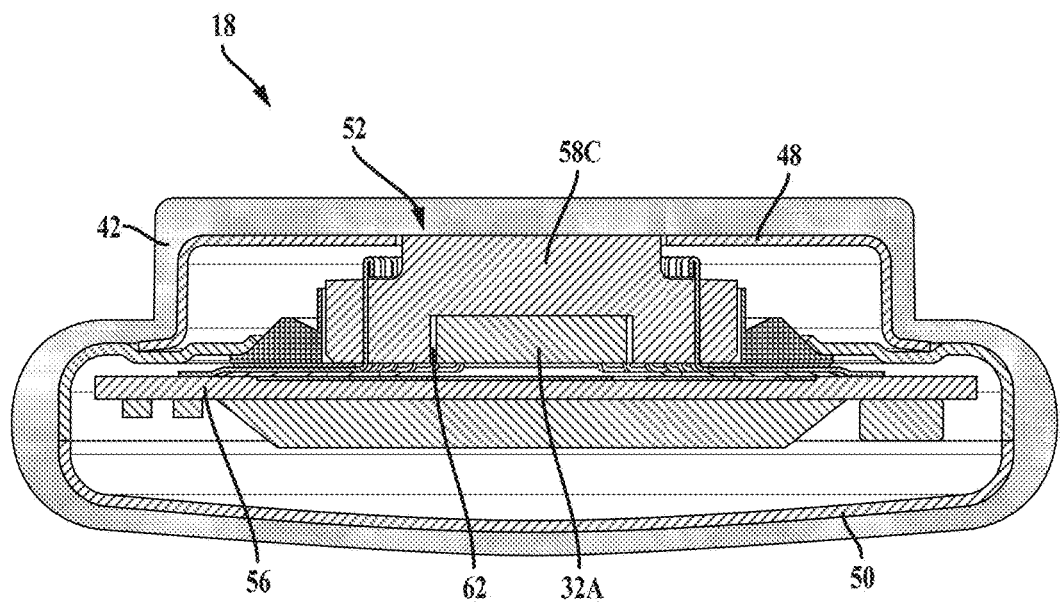
Figure 10:
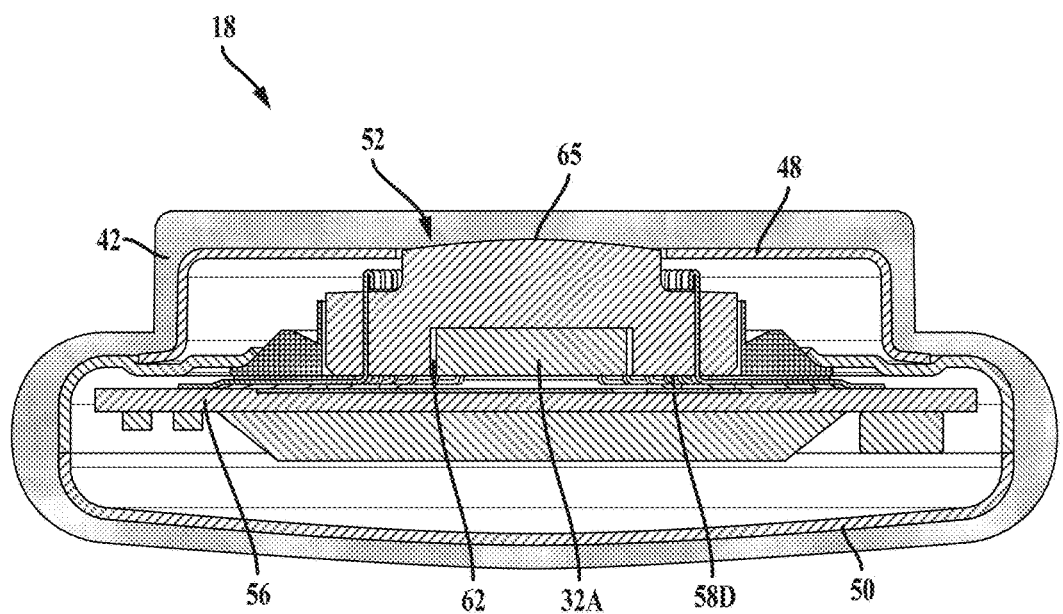

As another example, the feedthrough could be shaped to act as a waveguide for RF signals. FIGS. 9-12 show examples of such a feedthrough. For instance, FIG. 9 shows a third feedthrough 58C that extends into the aperture 58 such that an upper surface of the third feedthrough 58C is level with an upper surface of the anterior plate 48. In FIG. 10, a fourth feedthrough 58D includes a convex-curved upper surface 65. As shown, the curved upper surface 65 extends up to or over the upper surface of the anterior plate 48. The curved upper surface 65 may improve the hearing device's ability to communicate with the external device 12 by focus incoming RF signals to the first antenna element 32A while also directing outgoing RF signals.

Figure 11:
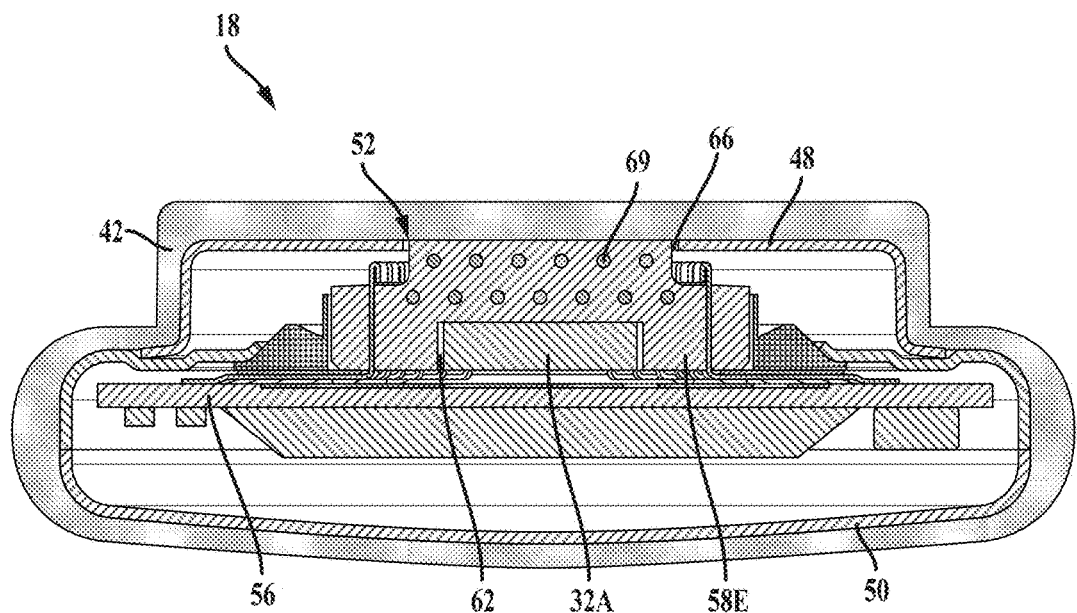
Figure 12:
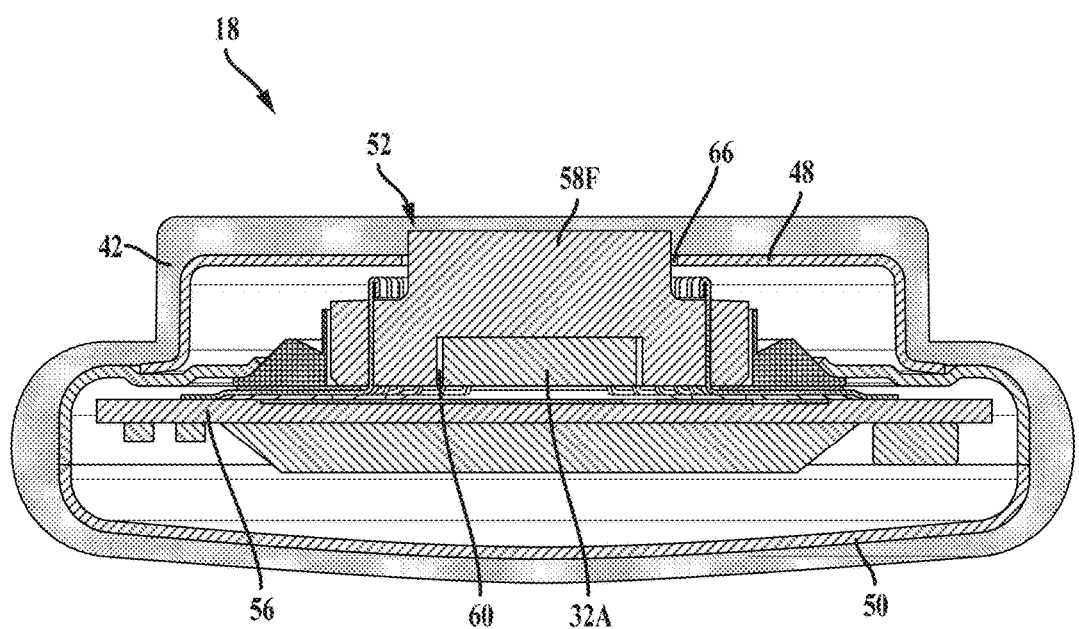
Figure 13:
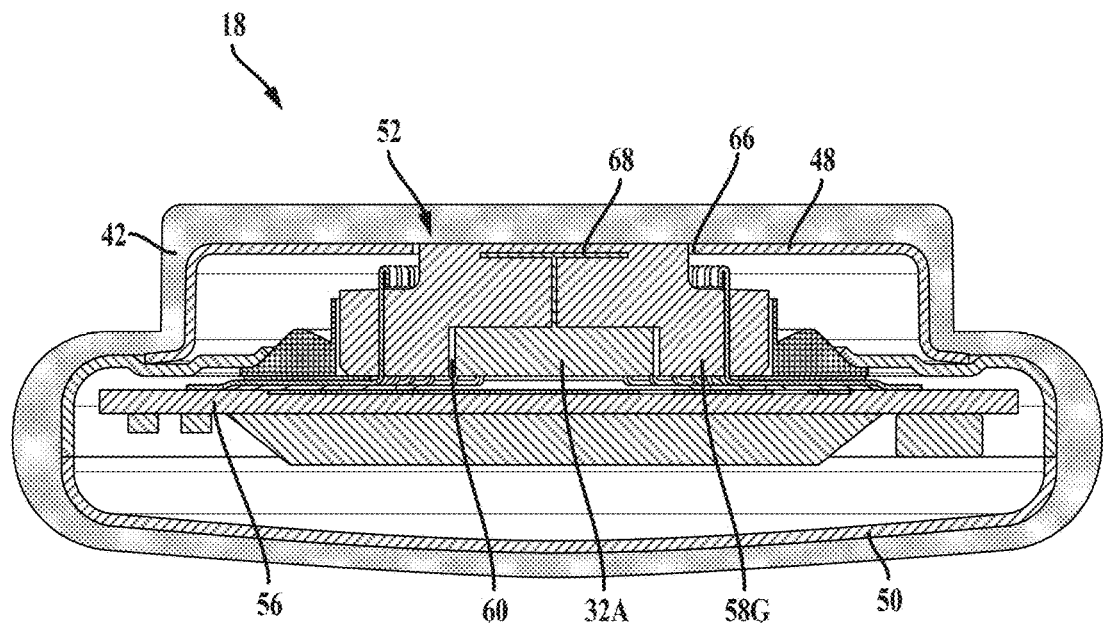

In FIG. 11, a fifth feedthrough 58E has the same shape as the third feedthrough 58C. The fifth feedthrough 58E could be fabricated such that small volumes 66 of differing dielectric or conducting materials are interspersed in the bulk material of the fifth feedthrough 58E. The small volumes 69 could be distributed throughout the fifth feedthrough 58E so as to have a positive guiding effect on RF signals. And as shown in FIG. 12, a sixth feedthrough 58F could extend past the anterior plate 48 such that an upper surface of the sixth feedthrough 58F is level with the polymer covering 42. In this example, the upper surface of the sixth feedthrough 58F could be polished so as to provide an essentially smooth surface, thereby minimizing the potential for biofilm growth on the sixth feedthrough 58F.

As yet another example, a portion of the antenna 32 could be incorporated into the feedthrough. FIG. 12 shows an embodiment in which an antenna element 68 is embedded in a seventh feedthrough 58G. Here, the antenna element 68 could be a directional antenna, such as a Yagi antenna, with the antenna element 68 having a diameter of about 4 millimeters and a thickness of about 0.1 millimeters. Mounting the seventh feedthrough 58G over the first antenna 32A could cause first antenna 32A to contact the antenna element 68, thereby creating a connection between the first antenna element 32A and the antenna element 68. Alternatively, the first antenna 32A, the seventh feedthrough 58G, and the antenna element 68 could be manufactured as a single element.

In the preceding examples, at least a portion of the feedthroughs 58A-58G are above the antenna 32 (i.e., closer to the anterior plate 48). Alternatively, the antenna 32 could be positioned above the feedthrough, as shown in FIGS. 14-18. Positioning the antenna 32 above the feedthrough may provide a higher antenna gain (as compared to the first antenna 32), as RF signals would not have to pass through the feedthrough and would not be as susceptible to interference from signals relayed to the stimulation component via the feedthrough.

Figure 14:
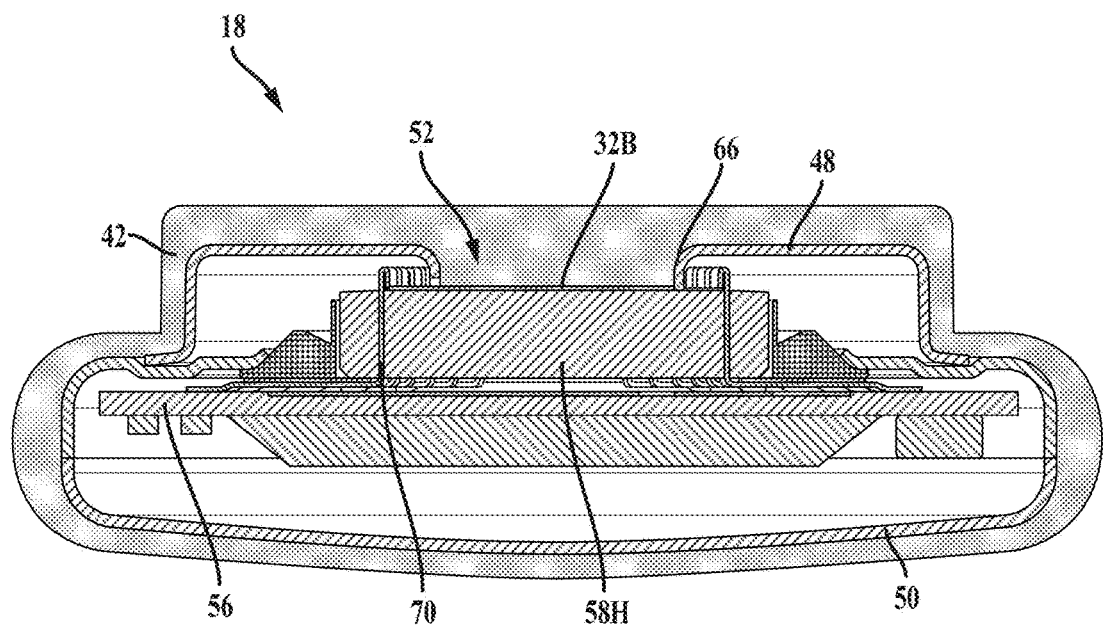

FIG. 14 shows an example in which an eighth feedthrough 58H is mounted to the printed circuit board 56, and a second antenna 32B is mounted on the eighth feedthrough 58H. The second antenna 32B in this example is connected to the printed circuit board 56 via a feedthrough pin 70, which could be the same as or substantially similar to the feedthrough pins used to connect the electrodes of the stimulation component 20 to the printed circuit board 34.

Figure 15:
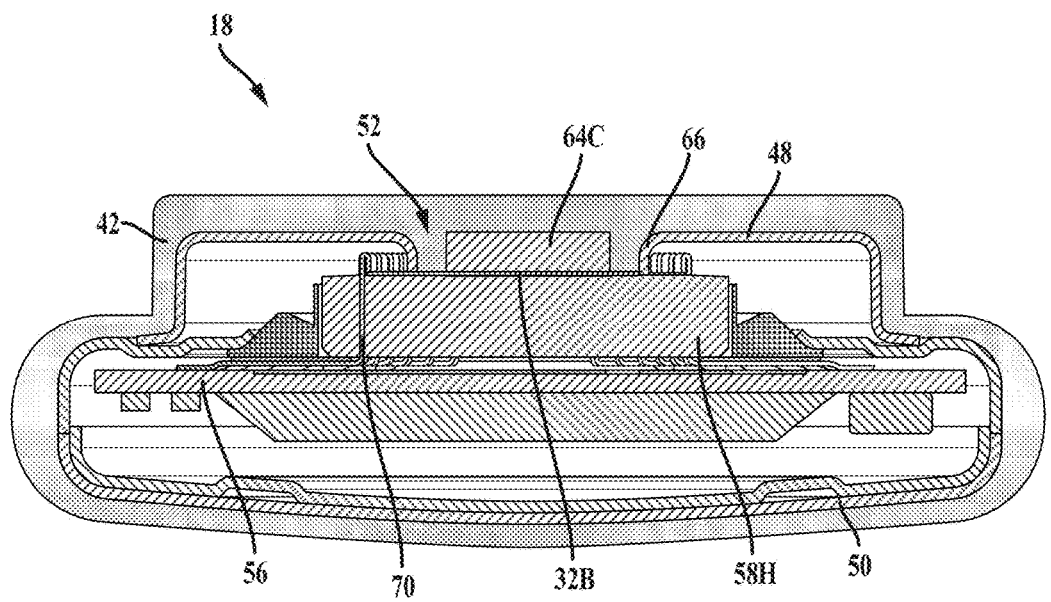
Figure 16:
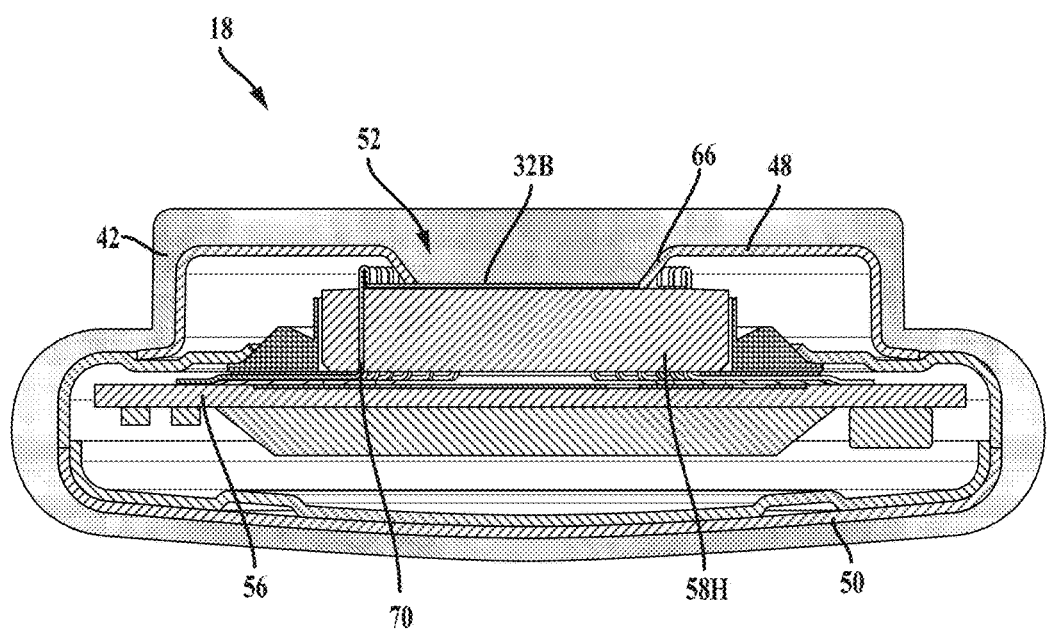
Figure 17:
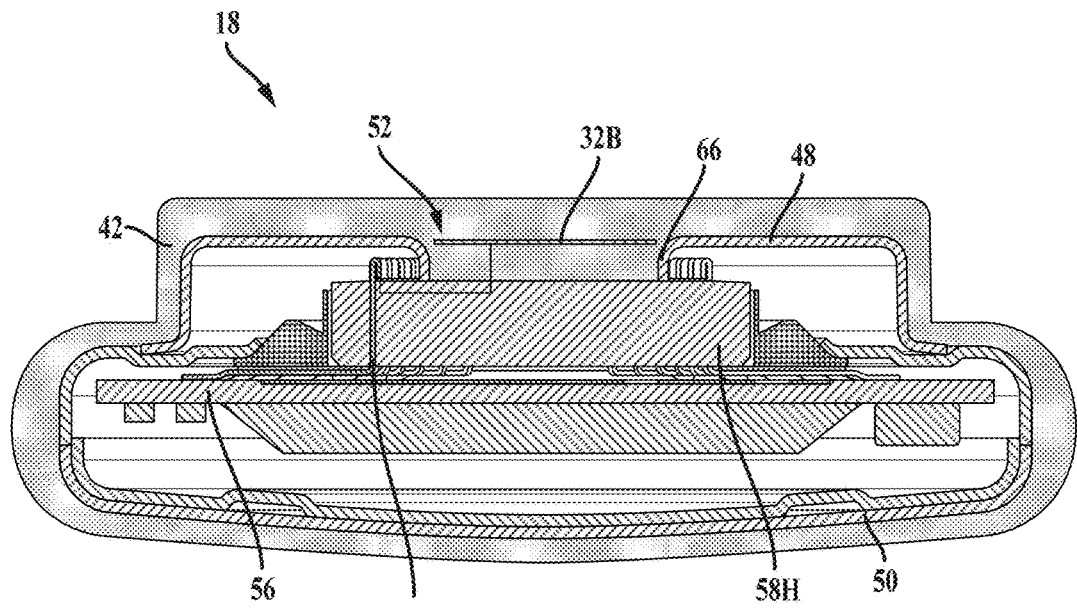
Figure 18:
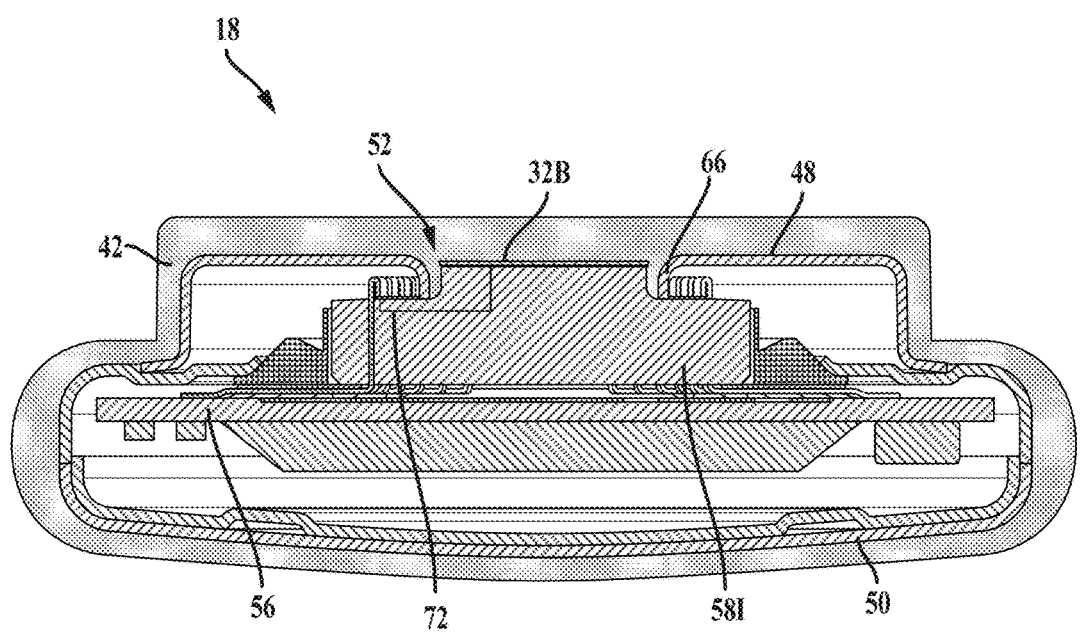

The example depicted in FIG. 14 can be modified to reduce the attenuation of RF signals transmitted and received via the second antenna 32B. In FIG. 15, for instance, a third waveguide 64C could be mounted on the second antenna 32B. Alternatively, the inner edge 66 of the anterior plate 48 could be angled, described with respect to FIG. 8. In yet another example, the second antenna 32B could be suspended in the polymer cover 42 such that the second antenna 32B is centered in the aperture 52, as shown in FIG. 17. And in FIG. 18, the second antenna 32B is mounted on a ninth element 58I, a portion of which could extend upward to the aperture 52 such that the second antenna 32B is level with the upper surface of the anterior plate 48. In the examples depicted in FIGS. 14-16, positioning the second antenna 32B near the top of the aperture 52 may reduce interference caused by RF signals passing through different media, such as the anterior plate 48 and the feedthrough 58I and 58H. However, because the antenna 32 may be on or near the aperture 52, which is an opening in the anterior plate 48, the second antenna element should be fabricated from biocompatible materials.

Figure 19:
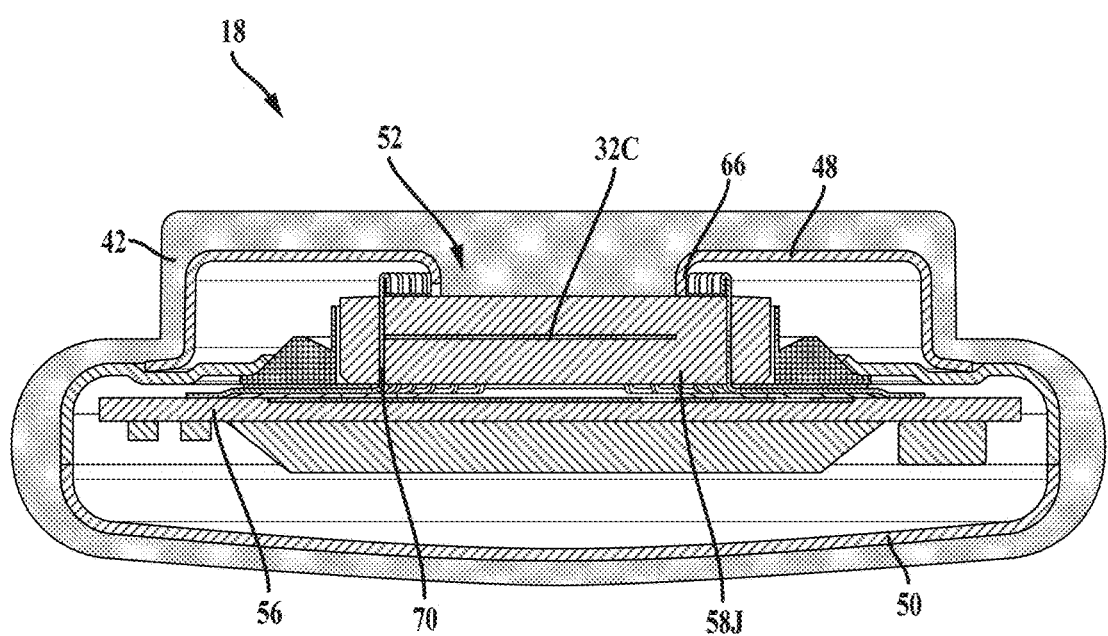

Finally, FIG. 19 shows a tenth feedthrough 58J. In this example, a third antenna 32C is embedded in the tenth feedthrough 58J. Like the examples depicted in FIGS. 14-18, the third antenna element 32C could be connected to the printed circuit board 56 via the feedthrough pin 70.

In the preceding examples, the aperture 52 is depicted as having a circular shape. In other examples, the aperture 52 could have a different shape. Similarly, while at least a portion of each of the feedthrough 58A-58J is depicted as having a cylindrical shape, the feedthrough could have a shape other than a cylinder. Further, the housing 18 could be configured such that the aperture 52 (or perhaps an additional aperture) is in the posterior plate 50. This particular example may be beneficial in bilateral hearing device systems, as the RF signals could be attenuated due to the signals radiating through the posterior plate and through the recipient's skull.

In the preceding example, the example feedthroughs and antennas described can take various forms. For instance, the feedthroughs could be about 9 millimeters in diameter and have a thickness between about 1.8 millimeters and about 4 millimeters. As for the antennas, the first antenna 32A could have a diameter of about 2 millimeters and thickness of about 1.5 millimeters, whereas the second antenna 32B and the third antenna 32C could have a diameter of about 4 millimeters and a thickness between 0.1 millimeters and 0.5 millimeters. Further, the diameters and thicknesses of the feedthrough, the antenna (or antenna elements), and/or other components of the housing 18 could differ from the example values based on the particular dimensions of the housing 18. A housing larger than the housing 18 described in the preceding examples may thus allow for larger components with larger diameters and/or thickness than the examples provided above, whereas a housing smaller than the housing 18 may require components that have dimension which are smaller than the example dimension. In each example described above, the housing 18 could be manufactured using any method or process for manufacturing implantable units of hearing devices that is now known or is later developed. Further, the components of and/or within the housing 18 could have different shapes than those of those of the example components described herein.

Thus, in line with the discussion above, an implantable medical device could comprise a housing having a posterior side and an anterior side, wherein the anterior side has an inner edge that defines an aperture. The implantable medical device could then include an electrical feedthrough made of one or more biocompatible materials that covers the aperture to form a hermetic enclosure within the housing, a receiver enabling RF communications, and an antenna element electrically connected to the receiver, with the antenna element positioned directly below, above, or inside the electrical feedthrough.

In such an arrangement, the receiver could be part of a transceiver, and a surface of the antenna element could be in physical contact with a surface of the electrical feedthrough. Further, the antenna element could be disposed within the hermetic enclosure between the electrical feedthrough and the posterior side of the housing. Moreover, the electrical feedthrough could be formed such that a posterior surface of feedthrough defines a recess, the electrical feedthrough could be mounted on a printed circuit board over the antenna element such that the antenna element is positioned within the recess, and a waveguide could be provided for channeling RF signals to and from the antenna element.

In addition, the anterior surface of the electrical feedthrough in such an implantable medical device could be curved, the antenna element could include a directional antenna element that is embedded in the electrical feedthrough. Further, the electrical feedthrough could be positioned between the antenna element and the posterior surface of the housing, the housing could be covered in a silicon molding, the antenna element could be suspended in the silicon molding, and a waveguide could be suspended in the silicone molding over the antenna element and the electrical feedthrough.

Still further, the inner edge of the anterior side of the implantable medical device could extend axially into the housing from an upper surface of the anterior side and could be angled toward a center of the aperture. And the feedthrough could comprise areas of different dielectric constants.

Also in line with the discussion above, a hearing prosthesis could comprise an electrode array implantable in a cochlea and a housing with electronic circuitry, including an RF transceiver, disposed therein, the housing having an aperture that is sealed by an electrical feedthrough to form a hermetic enclosure, the electrode array comprising a plurality of electrodes that are electrically connected to a component in the housing via the feedthrough, with one or more antenna elements electrically connected to the transceiver being positioned in-line with aperture. And at least one of the antenna elements could be embedded in the electrical feedthrough.

Moreover, an implantable medical device could comprise a hermetic enclosure that encases electronic circuitry, including a radio frequency transceiver, the hermetic enclosure comprising a metallic chassis with an aperture sealed by a non-metallic feedthrough, the radio frequency transceiver having an antenna element that is disposed in-line with the feedthrough.

In such an implantable medical device, the antenna element could be disposed inside the hermetic enclosure, and a surface of the antenna element could be in physical contact with an inner surface of the electrical feedthrough. Alternatively, the antenna element could be disposed outside the hermetic enclosure, and a surface of the antenna element is in physical contact with an outer surface of the electrical feedthrough. Further, the housing could be encapsulated in a polymer covering, and the antenna element could be suspended in the polymer covering so that the antenna is spaced from the feedthrough. Moreover, the antenna could be centered with respect to the aperture.

While various aspects and embodiments have been disclosed herein, other aspects and embodiments will be apparent to those skilled in the art. The various aspects and embodiments disclosed herein are for purposes of illustration and are not intended to be limiting, with the scope being indicated by the following claims.

What is claimed is:

1. An implantable medical device comprising:
   a housing, wherein a side of the housing defines an aperture;
   an electrical feedthrough made of one or more biocompatible materials that covers the aperture to form a hermetic enclosure with the housing;
   a receiver enabling radio frequency (RF) communications; and
   an antenna element electrically connected to the receiver, wherein the antenna element is positioned in-line with the electrical feedthrough.

2. The implantable medical device of claim 1, wherein the housing has a posterior side and an anterior side, and wherein the anterior side has an inner edge that defines the aperture.

3. The implantable medical device of claim 1, wherein the housing includes a chassis sidewall that defines the aperture.

4. The implantable medical device of claim 1, wherein the housing has a posterior side and an anterior side, and wherein the posterior side and anterior side are each made of a material different than the one or more biocompatible materials of the electrical feedthrough.

5. The implantable medical device of claim 1, wherein the antenna element is substantially concentric with the electrical feedthrough and is positioned directly below, above, or inside the electrical feedthrough to reduce attenuation of RF signals at least one of transmitted or received via the antenna.

6. The implantable medical device of claim 1, wherein the receiver is part of a transceiver.

7. The implantable medical device of claim 1, wherein a surface of the antenna element is in physical contact with a surface of the electrical feedthrough.

8. The implantable medical device of claim 1, wherein the housing has a posterior side and an anterior side, and wherein the antenna element is disposed within the hermetic enclosure between the electrical feedthrough and the posterior side of the housing.

9. The implantable medical device of claim 8, wherein the electrical feedthrough is formed such that a posterior surface of the feedthrough defines a recess, and wherein the electrical feedthrough is mounted on a printed circuit board over the antenna element such that the antenna element is positioned within the recess.

10. The implantable medical device of claim 8, further comprising a waveguide for channeling RF signals to and from the antenna element.

11. The implantable medical device of claim 1, wherein an anterior surface of the electrical feedthrough is curved.

12. The implantable medical device of claim 1, wherein the antenna element includes a directional antenna element that is embedded in the electrical feedthrough.

13. The implantable medical device of claim 1, wherein the housing has a posterior side and an anterior side, and wherein the electrical feedthrough is positioned between the antenna element and the posterior surface of the housing.

14. The implantable medical device of claim 1, wherein the housing is covered in a silicone molding, and wherein a waveguide is suspended in the silicone molding over the antenna element and the electrical feedthrough.

15. The implantable medical device of claim 1, wherein the housing is covered in a silicone molding, and wherein the antenna element is suspended in the silicone molding.

16. The implantable medical device of claim 1, wherein the housing has a posterior side and an anterior side, and wherein an inner edge of the anterior side extends axially into the housing from an upper surface of the anterior side.

17. The implantable medical device of claim 16, wherein the inner edge is angled toward a center of the aperture.

18. The implantable medical device of claim 1, wherein the feedthrough comprises areas of different dielectric constants.

19. The implantable medical device of claim 1, further comprising an electrode array implantable in a cochlea, the electrode array comprising a plurality of electrodes that are electrically connected to a component in the housing via the electrical feedthrough.

20. The implantable medical device of claim 1, wherein the housing is formed from one or more biocompatible materials that attenuate RF signals and the electrical feedthrough is formed from one or more biocompatible materials that are at least quasi-transparent to RF signals.

21. An implantable medical device, comprising:
   a hermetic enclosure comprising a metallic chassis with an aperture;
   a non-metallic feedthrough sealing the aperture; and
   electronic circuitry, including a radio frequency transceiver electrically connected to an antenna element that is disposed in-line with and at least one of directly above, below, or inside the feedthrough.

22. The implantable medical device of claim 21, wherein the antenna element is disposed inside the hermetic enclosure directly below the feedthrough.

23. The implantable medical device of claim 22, wherein a surface of the antenna element is in physical contact with an inner surface of the electrical feedthrough.

24. The implantable medical device of claim 21, wherein the antenna element is disposed outside the hermetic enclosure directly above the feedthrough.

25. The implantable medical device of claim 24, wherein a surface of the antenna element is in physical contact with an outer surface of the electrical feedthrough.

26. The implantable medical device of claim 24, wherein the housing is encapsulated in a polymer covering, and wherein the antenna element is suspended in the polymer covering so that the antenna is spaced from the feedthrough.

27. The implantable medical device of claim 21, wherein the antenna is substantially centered with respect to the aperture.

\* \* \* \* \*